(12) United States Patent
Saari

(10) Patent No.: US 8,434,694 B2
(45) Date of Patent: May 7, 2013

(54) DOOR MOUNTED ROOM DEODORIZER

(76) Inventor: Michael J. Saari, Bessemer, MI (US)

( * ) Notice: Subject to any disclaimer, the term of this patent is extended or adjusted under 35 U.S.C. 154(b) by 210 days.

(21) Appl. No.: 12/710,491

(22) Filed: Feb. 23, 2010

(65) Prior Publication Data
US 2011/0204158 A1  Aug. 25, 2011

(51) Int. Cl.
*A61L 9/04* (2006.01)
*A24F 25/00* (2006.01)
*A62C 31/28* (2006.01)
*B05B 15/00* (2006.01)
*B64D 15/10* (2006.01)

(52) U.S. Cl.
USPC ...... 239/60; 239/6; 239/34; 239/57; 239/274; 454/195

(58) Field of Classification Search .......... 239/6, 34, 239/57, 60, 274; 454/195
See application file for complete search history.

(56) References Cited

U.S. PATENT DOCUMENTS

| | | | |
|---|---|---|---|
| 4,040,568 A * | 8/1977 | Mason et al. | 239/57 |
| 4,615,486 A * | 10/1986 | Konicek | 239/274 |
| 4,903,584 A | 2/1990 | Styles | |
| 5,141,707 A | 8/1992 | Brite | |
| 5,422,078 A | 6/1995 | Colon | |
| 5,873,529 A * | 2/1999 | Johnson | 239/274 |
| 5,967,412 A * | 10/1999 | Lee | 239/57 |
| 6,123,906 A | 9/2000 | Farmer | |
| 6,190,607 B1 | 2/2001 | Farmer | |
| 6,386,971 B1 | 5/2002 | Johnson | |
| 2008/0061453 A1 | 3/2008 | Diaz | |
| 2011/0197766 A1* | 8/2011 | Bordin | 95/284 |

* cited by examiner

Primary Examiner — Ryan Reis
(74) Attorney, Agent, or Firm — Andrus, Sceales, Starke & Sawall, LLP

(57) ABSTRACT

A room deodorizer that utilizes an airflow created by a ventilation device within an enclosed room to disperse a deodorizing agent. The room deodorizer is mounted near the bottom edge of a door and includes a deodorizing strip that extends below the bottom edge of the door to the floor. The deodorizing strip obstructs an airflow passageway created between the bottom edge of the door and the floor. The deodorizing strip is impregnated with a deodorizing agent such that when a ventilation device within the room is activated, the created airflow passes through the deodorizing strip to release the deodorizing agent into the enclosed room.

8 Claims, 2 Drawing Sheets

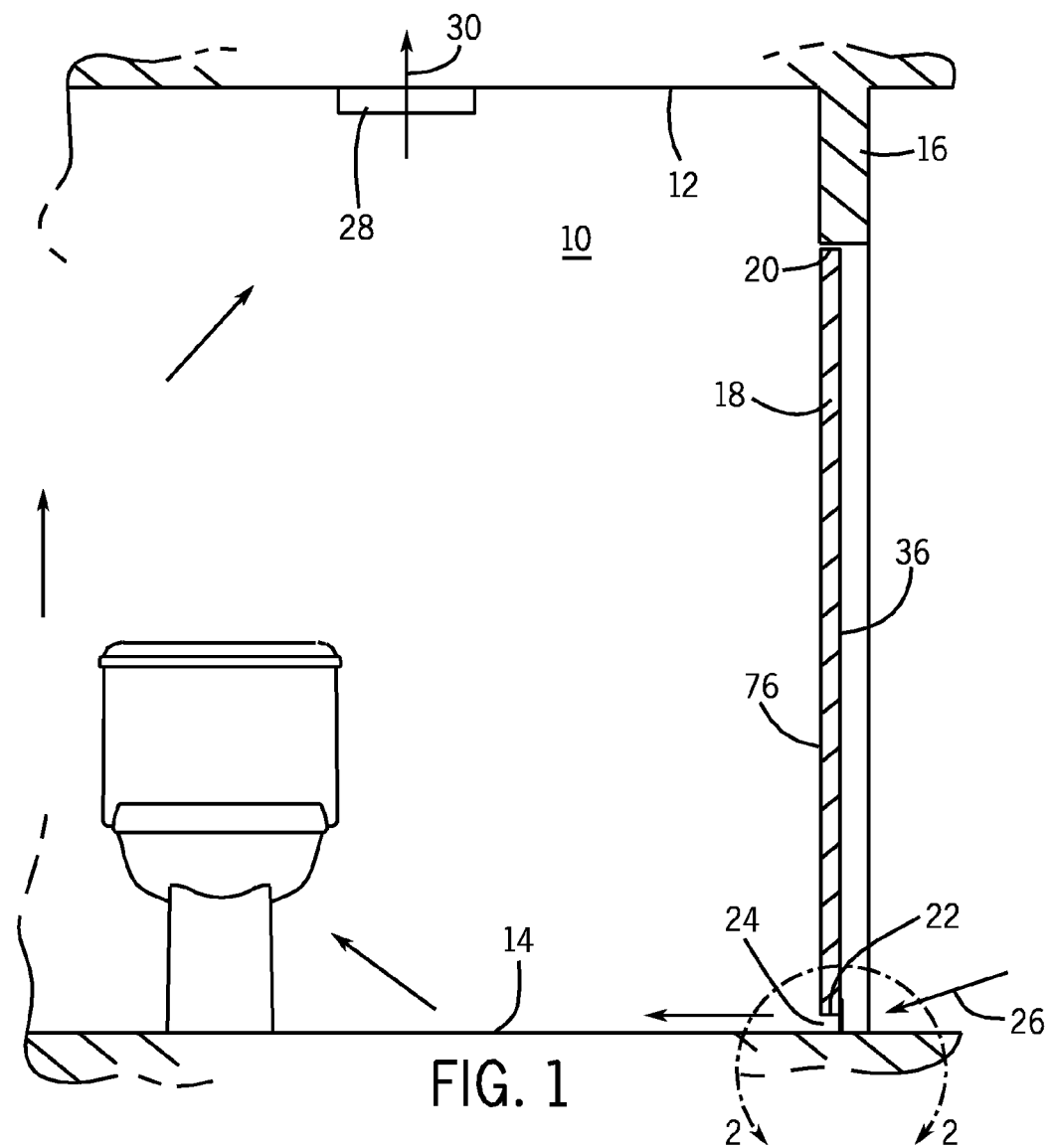
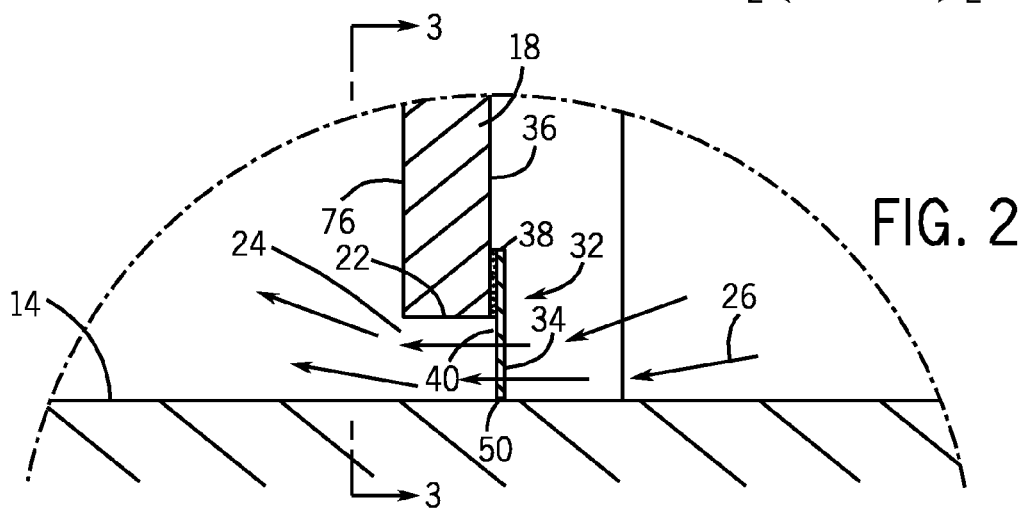

DOOR MOUNTED ROOM DEODORIZER

BACKGROUND OF THE INVENTION

The present disclosure generally relates to a room deodorizer. More specifically, the present disclosure relates to a room deodorizer that can be mounted to a door and disperses a deodorizing agent throughout the room as a result of an airflow created by a ventilation device within the room.

Small, enclosed rooms within a home, such as a bathroom, typically include some type of ventilation device that removes air from within the enclosed area. When the ventilation device is activated, air within the room is removed and fresh air is drawn into the enclosed room, which aids in removing odors and generally freshens the air within the enclosed room. In addition to ventilation devices, it is typical to utilize some type of spray air freshener to mask unpleasant odors within the enclosed room. Although spray air fresheners function well to mask unpleasant odors, spraying an air freshener within an enclosed room often causes the air freshener to be deposited over everything in the room, such as the mirror, towels and shelving. Further, spray air freshener requires a user to find the air freshener and manually use the air freshener Other types of air freshening devices are currently available that continuously dispense a deodorizing agent into air within an enclosed room. Although these devices function well, the devices dispense deodorizing agent even when the deodorizing agent is not required.

Therefore, a need exists for a room deodorizer that automatically activates when needed and can be replaced/replenished upon becoming depleted. Further, a need exists for a room deodorizer that is unobtrusive and functions to disperse deodorizing agent into the enclosed room.

SUMMARY OF THE INVENTION

The present disclosure relates to a room deodorizer that functions to release a deodorizing agent into an enclosed room. More specifically, the present disclosure relates to a room deodorizing device that releases the deodorizing agent into an airflow created by the activation of a ventilation device within the enclosed room.

The room deodorizer includes a deodorizing strip that is mounted to substantially obstruct an airflow passageway formed between a bottom edge of a door and a floor of the enclosed room. The deodorizing strip is impregnated with a deodorizing agent and is porous such that air can flow through the deodorizing strip. When air passes through the deodorizing strip, the impregnated deodorizing agent is released into the airflow to deodorize the enclosed room.

In one contemplated embodiment, the deodorizing strip is mounted to the door utilizing a releasable adhesive. The releasable adhesive secures the deodorizing strip in a desired location on the door such that a bottom edge of the deodorizing strip is placed in close proximity to the floor. When the ventilation device is activated, the ventilation device creates an airflow through the airflow passageway. This airflow passes through the deodorizing strip, causing the deodorizing agent to be released into the airflow. When the deodorizing agent in the deodorizing strip has been depleted, the entire deodorizing strip can be removed from the door and replaced with a new strip.

In another contemplated embodiment, the room deodorizer includes a fluid reservoir formed within the bottom end of the door. The fluid reservoir receives a supply of deodorizing agent. The deodorizing strip is mounted such that a top end of the deodorizing strip is contained within the deodorizing agent in the fluid reservoir. The deodorizing strip acts as a wick for the deodorizing agent such that the deodorizing strip is impregnated with the deodorizing agent. Airflow through the deodorizing strip again releases the deodorizing agent into the airflow within the enclosed room.

In yet another contemplated embodiment, the room deodorizer includes a housing mounted to the door. The housing defines a fluid reservoir and a top end of the deodorizing strip extends into the fluid reservoir. The deodorizing strip again acts as a wick such that the deodorizing agent is released into the airflow as air flows through the deodorizing strip.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure.

FIG. 1 is a schematic illustration of a room including a ventilation device and a room deodorizer of the present disclosure;

FIG. 2 is a magnified view of the area illustrated by line 2-2 of FIG. 1;

DETAILED DESCRIPTION OF THE INVENTION

Figure 3:
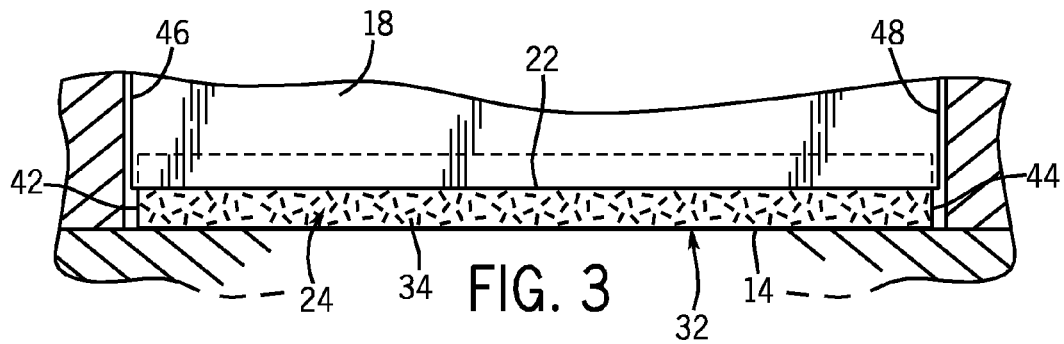
FIG. 3 is a view taken along line 3-3 of FIG. 2.

FIG. 1 illustrates an enclosed room 10, such as a bathroom, that includes a ceiling 12, a floor 14 and a series of walls 16. One of the walls includes a door 18 that can be selectively opened and closed. Door 18 is mounted in a doorway and extends between a top edge 20 and a bottom edge 22. The bottom edge 22 is spaced above the floor 14 to define an airflow passageway 24 that allows a flow of air 26 to enter into the enclosed room 10, as illustrated by arrows 26.

The enclosed room 10 includes a ventilation device 28 mounted within the ceiling 12. The ventilation device 28 is operable to exhaust air from within the enclosed room 10, as is illustrated by the exhaust airflow 30. Since the enclosed room 10 is generally sealed, the exhaust airflow 30 created by the ventilation device 28 creates the airflow 26. In the embodiment shown in FIG. 1, the ventilation device 28 is a conventional fan having a rotating blade that creates the exhaust airflow 30.

FIG. 2 illustrates a room deodorizer 32 constructed in accordance with the present disclosure. The room deodorizer 32 releases a deodorizing agent into the airflow 26 passing through the airflow passageway 24 formed between the bottom edge 22 of the door 18 and the floor 14. As described above, the airflow 26 is created by the operation of the ventilation device mounted within the ceiling 12. Thus, the room deodorizer 32 utilizes the induced airflow 26 to release the deodorizing agent when the ventilation device is activated.

In the embodiment shown in FIG. 2, the room deodorizer 32 includes a deodorizing strip 34 that is attached to an outer surface 36 of the door 18 by an attachment device. In the embodiment shown in FIG. 2, the attachment device is an adhesive 38. The adhesive 38 is applied to a portion of the back surface 40 of the deodorizing strip 34. The adhesive 38 allows the deodorizing strip 34 to be removably attached to the door 18.

As shown in FIG. 3, the deodorizing strip 34 has a length extending from a first end 42 to a second end 44. The length of the deodorizing strip 34 is approximately equal to the width of the door 18 between the spaced edge surfaces 46, 48. The deodorizing strip 34 can either be provided having the pre-cut length shown in FIG. 3 or, alternatively, the deodorizing strip can be provided having a length greater than the width of the door and the deodorizing strip 34 is then cut to the desired length. As can be seen in FIG. 3, when the room deodorizer 32 is mounted to the door 18, the deodorizing strip 34 substantially obstructs the airflow passageway 24 that is formed between the bottom edge 22 and the floor 14.

In the embodiment shown in FIGS. 2 and 3, the deodorizing strip 34 is formed from a non-woven material that is impregnated with a deodorizing agent. The deodorizing strip 34 is sufficiently porous to allow the airflow 26 to pass through the deodorizing strip 34. As the airflow passes through the deodorizing strip 34, the deodorizing agent impregnated within the deodorizing strip 34 is released into the airflow 26.

Referring back to FIG. 2, it is contemplated that the adhesive 38 could be a removable adhesive such that the room deodorizer 32 would be a disposable article. In such an embodiment, the deodorizing strip 34 would be supplied with the adhesive 38 formed as a strip along the back surface 40. Prior to installation onto the door 18, a release liner would cover the strip of adhesive 38 to maintain the tackiness of the adhesive before application. When a user desires to install the room deodorizer 32, the release liner is removed from the adhesive and the room deodorizer 32 is positioned as shown in FIG. 2. Preferably, the room deodorizer is positioned such that a bottom edge 50 of the deodorizing strip 34 either contacts the floor 14 or is positioned slightly above the floor. Since the ventilation device creates only a relative small airflow 26, it is desirable that the deodorizing strip 34 obstruct as much of the airflow passageway 24 as possible to direct as much of the airflow 26 through the porous deodorizing strip 34 as possible.

In the embodiment shown in FIGS. 2 and 3, when the impregnated deodorizing agent contained within the deodorizing strip 34 is depleted, the entire deodorizing strip 34 can be removed from the door 18 and another strip 34 attached thereto.

When a new deodorizing strip 34 is applied to the door 18, it is contemplated that the user would first cut the deodorizing strip 34 to length such that the length of the deodorizing strip closely matches the width of the door 18.

In the embodiment shown in FIGS. 2 and 3, the deodorizing strip 34 could be constructed of various different materials, each of which must be capable of retaining a deodorizing agent. The deodorizing strip 34 can be formed having various different colors, patterns or printed decorative images, as is desired.

Figure 4:
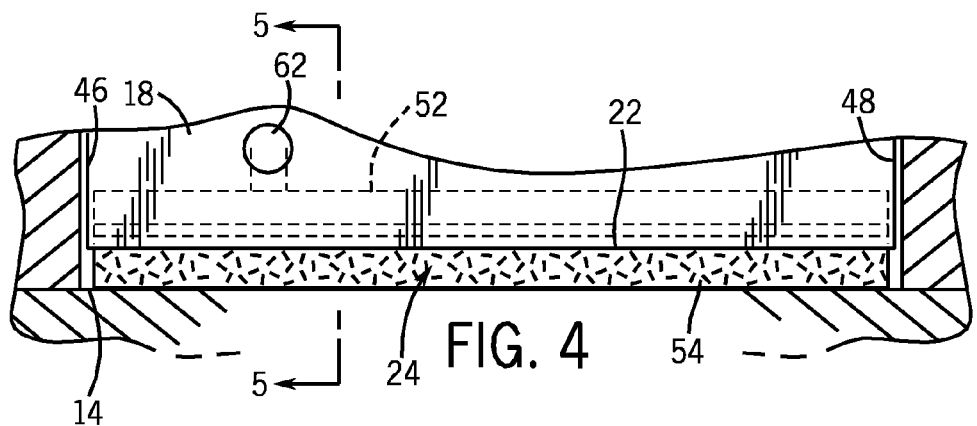
FIG. 4 is a view similar to FIG. 3 of an alternate configuration of the room deodorizer.
Figure 5:
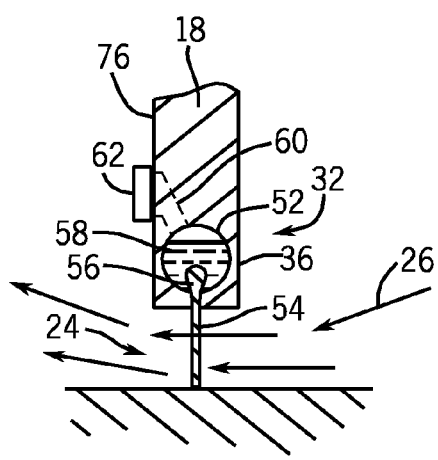
FIG. 5 is a section view taken along line 5-5 of FIG. 4.

Referring now to FIGS. 4 and 5, thereshown is an alternate embodiment of the room deodorizer 32. In the alternate embodiment, the room deodorizer 32 includes a fluid reservoir 52 formed within the body of the door 18. The fluid reservoir 52 is a self-contained, open reservoir that extends nearly the entire width of the door between the edge surfaces 46, 48. As shown in FIG. 5, the fluid reservoir 52 includes an opening formed near the lowermost portion of the fluid reservoir to receive the deodorizing strip 54. A top end 56 of the deodorizing strip 54 extends into the open interior defined by the fluid reservoir 52. As illustrated in FIG. 5, the top end 56 is immersed in the supply of deodorizing agent 58 contained within the fluid reservoir 52. The deodorizing strip 54 acts as a wick to impregnate the entire deodorizing strip 54 with the deodorizing agent.

As shown in FIGS. 4 and 5, the deodorizing strip 54 obstructs the airflow passageway 24 formed between the bottom edge 22 of the door 18 and the floor 14 in a similar manner as described in the first embodiment of FIGS. 1-3. Thus, as the airflow 26 is created by the operation of the ventilation device, the airflow 26 passes through the deodorizing strip 54 to release the deodorizing agent into the enclosed room.

In the embodiment shown in FIG. 5, the fluid reservoir 52 can be filled with the supply of deodorizing agent 58 through a fill port 60. The fill port 60 is closed by a removable cap 62. When the supply of the deodorizing agent 58 is depleted, the cap 62 is removed and additional deodorizing agent can be transferred into the fluid reservoir 52 through the fill port 60. The embodiment shown in FIGS. 4 and 5 requires the fluid reservoir 52 to be formed within the door body.

Figure 6:
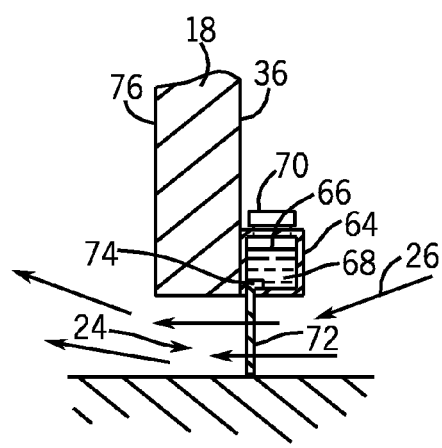
FIG. 6 is a section view similar to FIG. 5 of yet another embodiment of the present disclosure.

FIG. 6 illustrates another alternate embodiment constructed in accordance with the present disclosure. In the embodiment shown in FIG. 6, a housing 64 is attached to the outer surface 36 of the door 18. The housing 64 defines a fluid reservoir 66 that receives a supply of deodorizing agent 68. The housing 64 includes a removable cap 70 such that the supply of deodorizing agent can be replenished within the fluid reservoir 66.

A deodorizing strip 72 is positioned such that a top end 74 is immersed in the supply of deodorizing agent 68. The deodorizing strip 72 again acts as a wick to impregnate the deodorizing strip 72 with the deodorizing agent. As with the embodiment shown in FIGS. 4 and 5, the housing 64 has a length approximately equal to the width of the door such that the deodorizing strip 72 substantially obstructs the airflow passageway 24. In the embodiment shown in FIG. 6, the housing 64 can be secured to the door 18 using any one of numerous attachment techniques, such as an adhesive, mechanical fasteners or the like.

In the embodiments shown in the drawing Figures, each of the room deodorizers 32 are shown attached to an outer surface 36 of the door 18. However, it is contemplated that the room deodorizer could be mounted to an inner surface 76 while operating within the scope of the present disclosure.

Referring back to FIG. 2, in the embodiment shown, the bottom edge 22 of the door 18 is spaced from the floor 14 to define the airflow passageway 24. Typically, the bottom edge 22 is spaced above the floor 14 by approximately ½ inch. However, the spacing between the bottom edge 22 and the floor 14 could range between ⅛ inch to 1½ inch, depending upon the home construction. Therefore, the deodorizing strip 34 is formed having a height of approximately 2 inches to ensure that the deodorizing strip 34 can extend to cover the entire airflow passageway 24. The position of the deodorizing strip 34 relative to the door 18 can be adjusted to ensure that the bottom edge 50 contacts the floor 14, as described.

I claim:

1. A room deodorizer for mounting to a door having a width and a bottom edge spaced from a floor to define an airflow passageway, the room deodorizer comprising:
 a deodorizing strip impregnated with a deodorizing agent and having a length substantially equal to the width of the door; and
 an attachment device that secures the deodorizing strip to the door such that the deodorizing strip extends below the bottom edge of the door and substantially obstructs the airflow passageway along substantially the entire width of the door such that airflow through the airflow passageway must pass through the deodorizing strip when the door is in a closed position, wherein the attachment device is an adhesive applied to a back surface of the deodorizing strip.

2. The room deodorizer of claim 1 wherein the deodorizing strip has a height greater than a height of the airflow passageway.

3. The room deodorizer of claim 1 wherein the deodorizing strip is positioned on the door such that a bottom edge of the deodorizing strip contacts the floor.

4. The room deodorizer of claim 1 wherein the adhesive is a releasable adhesive such that the deodorizing strip is removable from the door without damaging the door.

5. The room deodorizer of claim 1 wherein the deodorizing strip is formed from a non-woven fabric.

6. A room deodorizer for mounting to a door having a width and a bottom edge spaced from a floor to define an airflow passageway having a height, the room deodorizer comprising:

a deodorizing strip having a height greater than the height of the airflow passageway and a width substantially equal to the width of the door; and an adhesive applied to a back surface of the deodorizing strip, wherein the deodorizing strip is attached to the door by the adhesive and positioned such that the deodorizing strip extends below the bottom edge of the door and substantially obstructs the airflow passageway along substantially the entire width of the door such that airflow through the airflow passageway must pass through the deodorizing strip when the door is in a closed position.

7. The room deodorizer of claim 6 wherein the deodorizing strip is impregnated with a deodorizing agent.

8. The room deodorizer of claim 6 wherein the adhesive is a releasable adhesive such that the deodorizing strip can be removed from the door without damaging the door.

* * * * *